United States Patent
Hauri et al.

(10) Patent No.: US 6,554,837 B1
(45) Date of Patent: Apr. 29, 2003

(54) DEVICE AND METHOD FOR INSERTING A PROSTHETIC KNEE

(75) Inventors: Bernard Hauri, Stafferbach (CH); Thomas Hauri, Staffelbach (CH); Werner Berner, Erlinsbach (CH)

(73) Assignee: Plus Endoprothetik AG, Rotkruez (CH)

( * ) Notice: Subject to any disclaimer, the term of this patent is extended or adjusted under 35 U.S.C. 154(b) by 0 days.

(21) Appl. No.: 09/719,109

(22) PCT Filed: Jun. 29, 1998

(86) PCT No.: PCT/CH98/00280

§ 371 (c)(1), (2), (4) Date: Feb. 13, 2001

(87) PCT Pub. No.: WO00/00093

PCT Pub. Date: Jan. 6, 2000

(51) Int. Cl.[7] .................................................. A61F 5/00
(52) U.S. Cl. ........................................................ 606/87
(58) Field of Search ............................ 606/87, 88, 89, 606/82

(56) References Cited

U.S. PATENT DOCUMENTS

| | | | |
|---|---|---|---|
| 4,457,307 A | | 7/1984 | Stillwell |
| 4,574,794 A | * | 3/1986 | Cooke et al. ................... 128/92 |
| 5,364,401 A | * | 11/1994 | Ferrante et al. ................ 606/84 |
| 5,514,143 A | | 5/1996 | Bonutti et al. |
| 5,649,928 A | * | 7/1997 | Grundei .......................... 606/88 |
| 6,013,081 A | * | 1/2000 | Burkinshaw et al. ........... 606/88 |

FOREIGN PATENT DOCUMENTS

| | | |
|---|---|---|
| EP | 0 322 363 A | 6/1989 |
| EP | 0 691 110 A | 1/1996 |
| EP | 0 709 061 A | 5/1996 |
| FR | 2 679 766 | 2/1993 |
| WO | WO 94/08528 | 4/1994 |

* cited by examiner

Primary Examiner—Eduardo C. Robert
(74) Attorney, Agent, or Firm—Oliff & Berridge, PLC

(57) ABSTRACT

A device for localizing and executing resection cuts on the femur (1) for preparing an implantation of a total endoprosthetic knee joint is provided. The device includes a reference device (5) adapted to be releasably attachable to the femur (1) in the distal area of the femur (1). Alignment of the reference device (5) relative to the femur (1) should be accurately positionable. An adjustment device (10) is connected to the reference device (5). The adjustment device (10) is movable relative to the reference device (5) and is provided with a linearly movable base part (10g) for the attachment of an instrument (11, 14). A first drive device (5v, 21) linearly moves the adjustment device (10) relative to the reference device (5) in the direction (10b) of a first axis (X) of a system of coordinates (X, Y, Z). A second drive device (10f, 17) linearly moves the base part (10g) in the direction (10d) of another, second axis (Y) of said system of coordinates (X, Y, Z). Both the first and second drive devices (5v, 21; 10f, 17) include a motor drive.

32 Claims, 12 Drawing Sheets

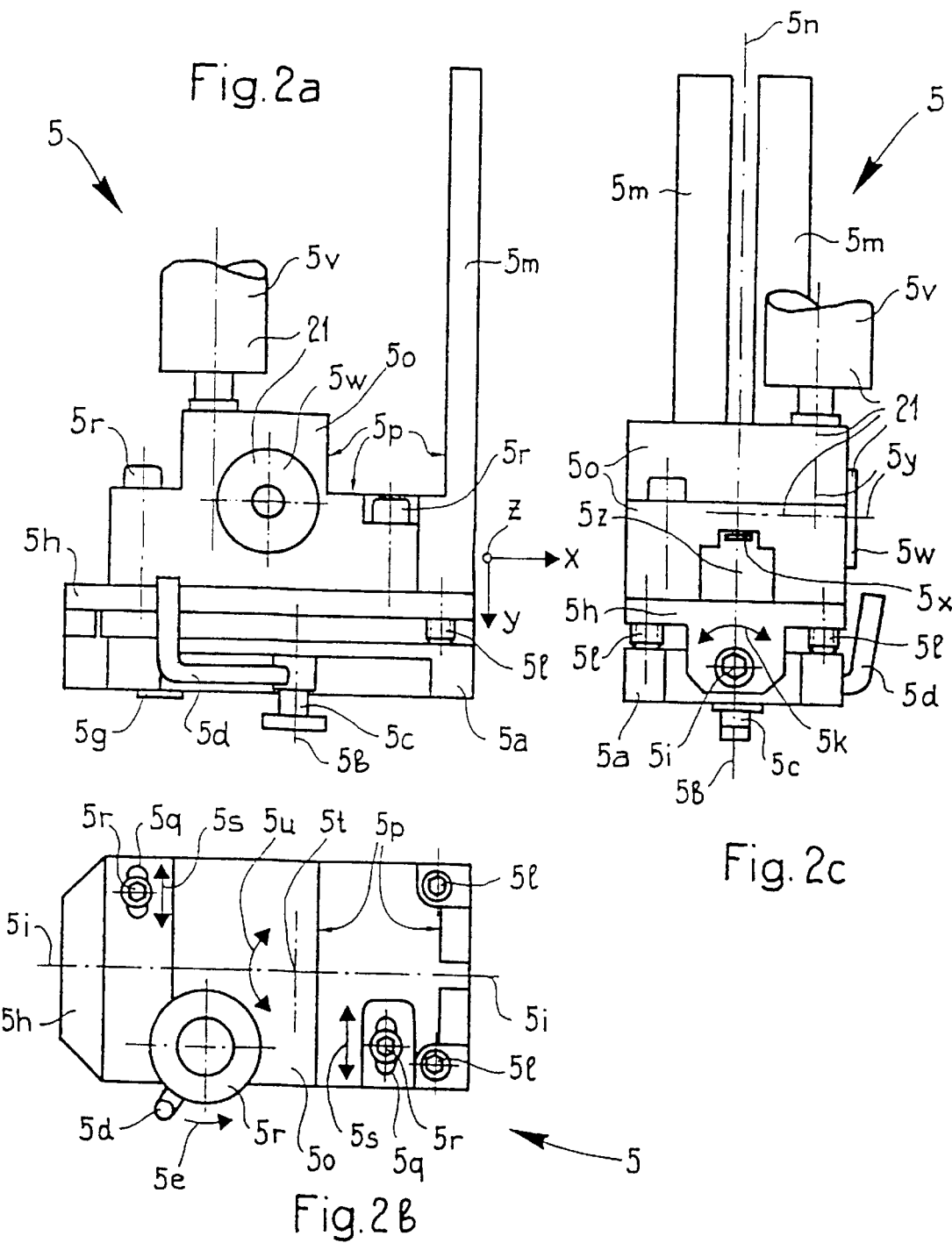

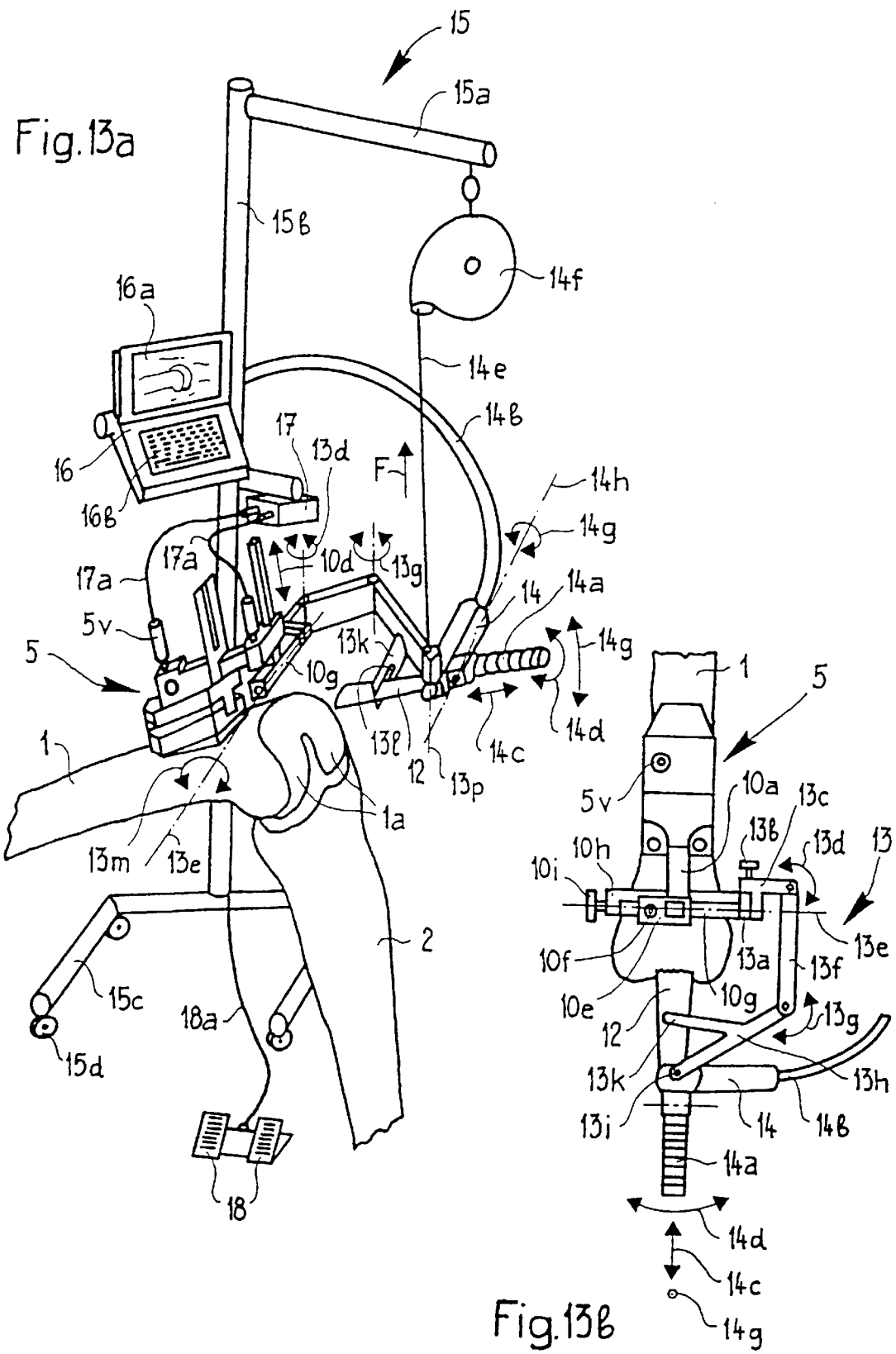

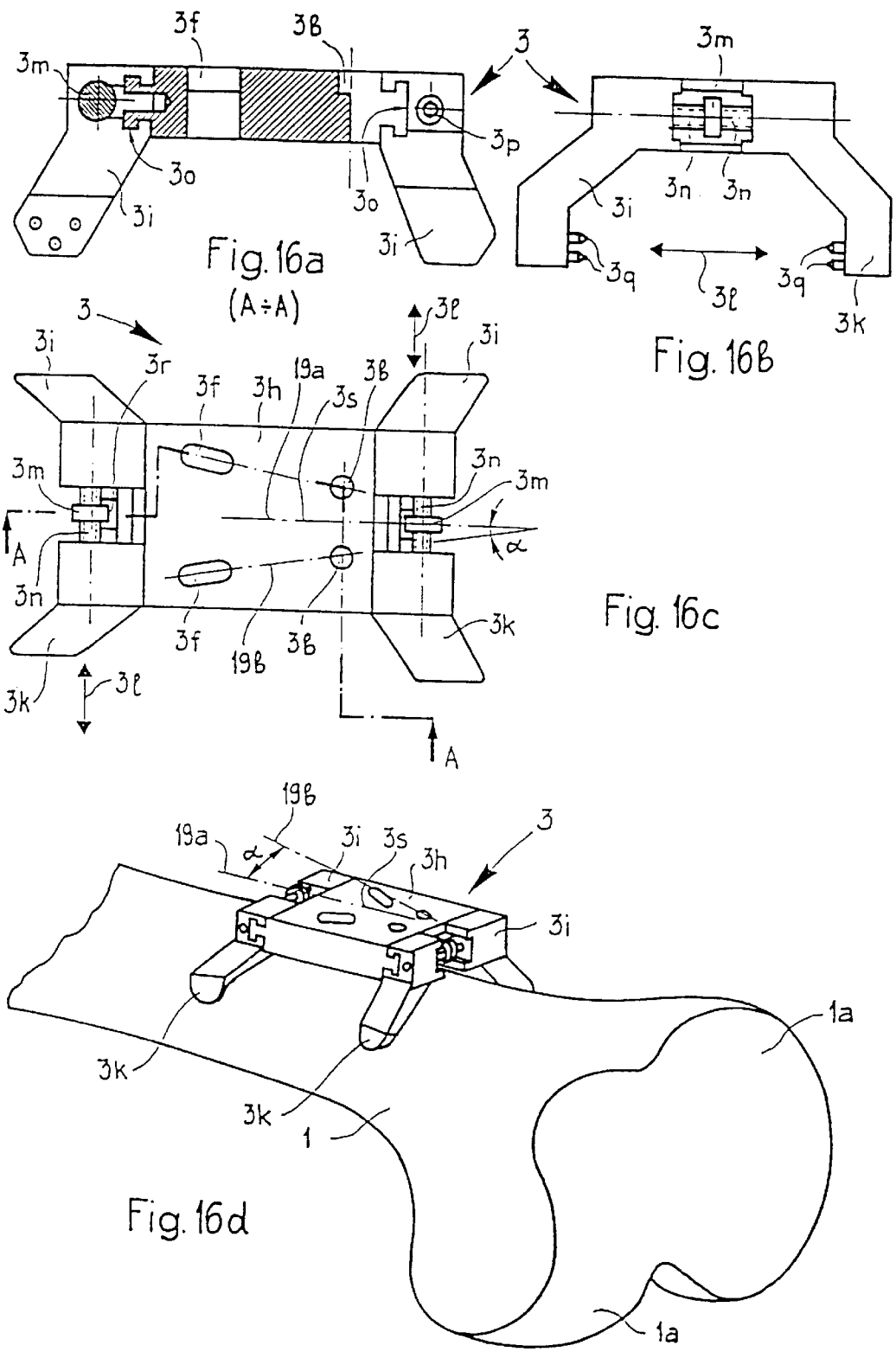

DEVICE AND METHOD FOR INSERTING A PROSTHETIC KNEE

The present invention relates to a device and to a method which allow a surgeon, when implanting a total endoprosthetic knee joint, to execute resection of the femur and of the tibia in an extremely precise manner.

The exact position of the resection lines on femur and tibia is of crucial importance for a long useful life of a total endoprosthetic knee joint. To date, resection has been extremely demanding, even for an experienced surgeon, since it is necessary, by means of the operation, to create the normal bearing surfaces according to the predetermined geometry of the endoprosthesis, in so doing to align the normal bearing surfaces according to the desired mechanical leg axes, if appropriate also correcting pathological defects of position, and in addition to take into account the position and the effect of the ligaments and muscles which are present. The alignment of tibia and femur is usually carried out by visual examination with the possible use of intramedullary or extramedullary aids, in which case an additional problem is that access to the operating field is often made difficult. These marginal circumstances can cause stressful situations even for surgeons with considerable experience.

A total endoprosthetic knee joint consists of a component secured to the femur and of a component secured to the tibia. Before the total endoprosthetic knee joint can be implanted, the adjoining bone areas of the femur and of the tibia must be appropriately resected in order to create normal bearing surfaces corresponding to the geometry of the endoprostheses. The frontal surfaces of the tibia and of the femur are usually resected. At least the femur is additionally provided with a so-called dorsal cut and a ventral cut since the femoral part of total endoprostheses is usually unshaped. The instruments generally supplied by manufacturers of prosthetic knees do not allow the necessary bone cuts on femur and tibia to be made with the required precision.

A further important requirement, however, is to ensure that those components of the prosthetic knee which slide on each other during flexion and extension of the knee are always in the correct position relative to each other, i.e. that the mechanical leg axis can deviate by not more than 3° varus or 3° valgus from the physiological bone axis, the deviation preferably being less than ±2°. In addition, it must also be borne in mind that the flexible connection between the two components is caused by ligaments and muscles, insofar as these are preserved upon implantation of the prosthesis. This requires equilibration of the ligament apparatus, ensuring good stability of the knee joint both in extension and in flexion.

The known instruments for implantation of total endoprosthetic knee joints generally comprise the following means:

means for aligning the tibia relative to the femur in order to obtain the desired leg axis position;

means for producing the desired tensioning of the knee ligaments;

means for performing resection of tibia and femur, in the form of sawing jigs which serve to guide a saw blade.

Such an instrument is known from the printed specification EP 0 322 363 A1. This instrument uses an extramedullary means for alignment of tibia and femur (extramedullary alignment system) and has the disadvantage that the alignment of the femur can be determined only with the aid of an X-ray apparatus. In addition, the reference system for the bone cuts is put in place by sight, said reference system additionally making access to the operating field difficult.

A further instrument is known from the printed specification EP 0 691 110 A2. This instrument uses an intramedullary means for alignment of tibia and femur (intramedullary alignment system) and has the disadvantage that a guide bar is in each case needed for mutual fixation of tibia and femur, said guide bar being introduced into medullary space of the tibia and femur, respectively. This intervention in the medullary space can cause thromboses and embolisms, with a possibly fatal outcome.

The object of the present invention is to make available a device and a method for localizing resection cuts on the femur and on the tibia for preparing an implantation of a total endoprosthetic knee joint, which method can be performed easily and in a reliably reproducible manner.

This object is achieved with a device having the features of claim 1, 15 or 23. The dependent claims 2 to 14, 16 to 22, and 24 to 36, relate to further advantageous embodiments of the device according to the invention. The object is also achieved with a method having the features of claim 37.

In an advantageous embodiment, the device according to the invention comprises a reference device consisting essentially of a base part which can be detachably locked in the distal area of the femur and of a reference body which is connected to the base part in an articulated and/or displaceable manner, which reference body has means defining a system of coordinates X, Y, Z, where the alignment of the reference body can be accurately positioned relative to the femur and where an actuating means acting between the reference body and the base part is provided for fixing the mutual position thereof, and where the means defining the system of coordinates X, Y, Z are designed for aligned attachment of working means such as a sawing jig, a base bar or a measurement device.

An advantage of this device is that the reference device is connected securely to the femur and is preferably aligned in the direction of extent of the weight-bearing axis of the femur, and that all the cuts on femur and tibia are carried out aligned relative to this reference system so that resection cuts or resection surfaces can be formed on the femur and tibia with very great precision and in a defined alignment.

The reference device can be secured on the femur by a large number of differently designed means, for example with bone screws, or with gripper arms which at least partially enclose the femur and can additionally have spikes which penetrate into the femur for improved anchoring.

In another advantageous embodiment, the device according to the invention comprises a reference device which can be secured extramedullarly and detachably in the distal area of the femur and whose alignment can be accurately positioned relative to the femur, and comprising a tibial splint which can be secured extramedullarly and detachably on the tibia, where the alignment of the tibial splint can be accurately positioned relative to the tibia, and comprising a securing device which securely connects the reference device and the tibial splint in a detachable manner.

This embodiment according to the invention has the advantage that the tibia can be brought into a precisely defined position relative to the femur and can then be fixed in this position. The direction of extent of the resection cuts on the tibia can therefore be predetermined by the cutting device secured on the femur. The position of the tibia can be accurately adjusted relative to the femur, for example in order to correct the line of the mechanical leg axis. In one advantageous embodiment, the securing device is of U-shaped or rectangular design, so that the operating area on the knee is by and large freely accessible even when the securing device is in place.

In a further advantageous embodiment, the device according to the invention comprises a reference device which can be detachably locked on the distal area of the femur and whose alignment can be accurately positioned relative to the femur, and a cutting device which is movably connected to the reference device, in particular a sawing jig for guiding a saw blade, or a sawing device having a saw blade, where the alignment of the cutting device, in particular of the saw blade, is determined at least by the alignment of the reference device. It is possible to use cutting devices with very different cutting methods, for example saws, ultrasonic cutting devices, or use of lasers. The device according to the invention allows the cutting device to be guided in such a way that the cut extends in the intended direction. An advantageous method for generating the cut has proven to be the use of a saw.

In a particularly advantageous embodiment, the sawing device comprises a saw blade whose extent defines a saw blade plane, the sawing device being secured with a connection means on the reference device and on the adjustment device, and the connection means and the sawing device being designed in such a way that the saw blade is mounted so as to be displaceable exclusively in the saw blade plane.

This embodiment has the advantage that the alignment of the saw blade is predetermined so that the operating surgeon can concentrate exclusively on moving the saw blade toward the bone and executing the resection, in the certainty that the alignment of the resection plane is correct. This makes things considerably easier for the operating surgeon during resection since he can concentrate essentially on the cutting, and in so doing can concentrate on any obstacles such as ligaments, and without having to worry about the direction of extent of the saw.

The device according to the invention can also be driven by a motor. In addition, a computer can be provided which monitors or even controls the movement of the device and the cutting.

The method according to the invention for performing resection cuts on femur or tibia is carried out in particular by means of a reference device being fixed on the distal area of the femur and then aligned relative to the direction of extent of the femur, and by means of a sawing jig, for guiding a saw blade, or a sawing device with a saw blade, being connected displaceably to the aligned reference device and being guided in an alignment defining the direction of extent of the resection cut, and by means of the resection being performed with the saw blade guided in alignment.

The invention is described below with reference to illustrative embodiments. In the drawings:

FIG. 2a shows a side view of a reference device;

FIG. 2b shows a plan view of a reference device;

FIG. 2c shows a rear view of a reference device;

FIG. 13a shows a perspective view of a total system for inserting a knee prosthesis;

FIG. 13b shows a plan view of a reference device and a cutting device secured thereon;

FIGS. 16a–16d show a further illustrative embodiment of a base plate to be secured on the femur.

In the following, the same components are provided with the same reference labels.

An essential feature of the device according to the invention and of the method according to the invention for insertion of a total endoprosthetic knee joint is the use of a reference system which can be anchored on the femur 1. This reference system is used as a reference for all the maneuvers and method steps for aligning the tibia 2 relative to the femur 1 and for performing resection on the articular surfaces. In an advantageous embodiment, the reference system anchored on the femur 1 can be adjusted in its alignment relative to the femur 1 in order to align the reference system in particular such that it runs in the weight-bearing direction of the femur 1.

Figure 1A:
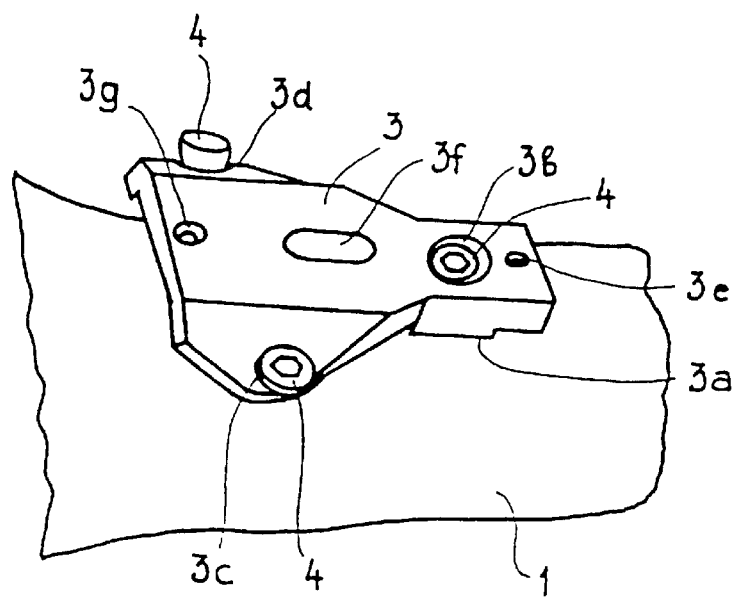
FIG. 1a shows a perspective view of a base plate secured on the femur.
Figure 1B:
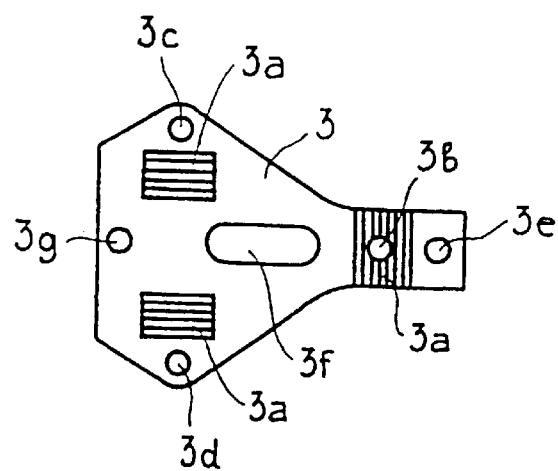
FIG. 1b shows a bottom view of a base plate.

FIG. 1a shows a base plate 3 which has bores 3b, 3c, 3d for receiving bone screws 4. As can be seen from the bottom view in FIG. 1b, the base plate 3 has three bearing surfaces 3a which are spaced apart from each other and which come to lie on the femur 1 so that the three-point contact thus formed guarantees a tilt-free bearing on the femur 1. The base plate 3 additionally has an opening 3f for receiving a bayonet catch and two alignment bores 3e, 3g. The bore 3b additionally has a countersink, as is shown in FIG. 1a.

Figure 3:
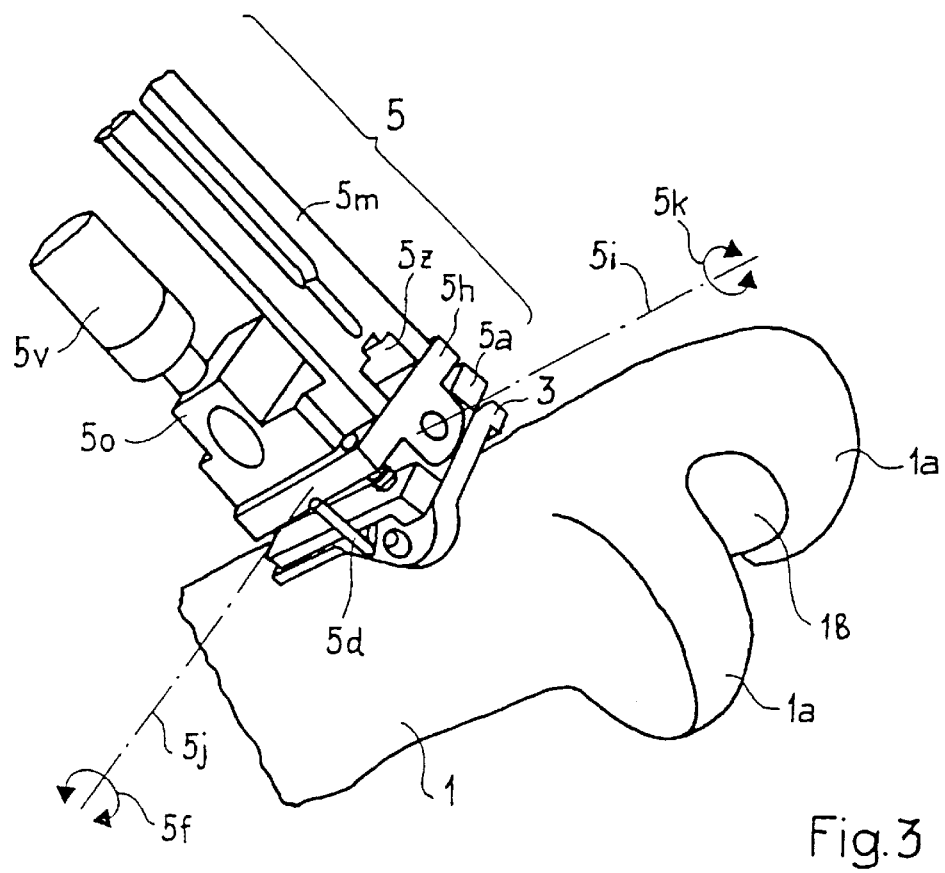
FIG. 3 shows a perspective view of a reference device secured on the femur.

As is shown in FIG. 3, the base plate 3 is arranged in the vicinity of the condyles 1a and aligned on the femur 1 in such a way that the axis formed by the bores 3g, 3e preferably extends in the direction of the weight-bearing axis 19b of the femur 1. For this purpose, a drilling gauge is used to fit two Steinmann nails into the femur 1, approximately in the direction of extent of the weight-bearing axis 19b, and the base plate 3 is then placed on the femur 1 in such a way that a Steinmann nail in each case extends through the bores 3g, 3e. A drilling jig is then placed on the bores 3b, 3c, 3d of the base plate 3, after which holes are drilled in the femur 1 and bone screws 4 are then introduced, so that the base plate 3, extending in its longitudinal extent approximately in the direction of the weight-bearing axis 19b, is securely connected to the femur 1 by the bone screws 4.

In a preferred embodiment, the device according to the invention has a reference device 5 which can be connected securely to the base plate 3, the mutual position of base plate 3 and reference device 5 being adjustable in order to set the course of the resection lines on femur and tibia as exactly as possible. FIGS. 2a to 2c show such a reference device 5 which has component elements whose alignments define a system of coordinates X, Y, Z, in relation to which system of coordinates all other maneuvers and cuts on femur 1 and tibia 2 are made.

The reference device 5 comprises a base part 5a on which a closure part 5c of a bayonet catch with pivot axis 5b and actuating lever 5d is arranged. The base part 5a is connected to the base plate 3 in such a way that the lever 5d is brought into the position illustrated, after which the closure part 5c is introduced into the opening 3f and the locking part 5g is then introduced into the countersink of the bore 3b. The actuating lever 5d is then moved in the direction 5e so that the bayonet catch formed by the parts 5c, 3f is locked and the base part 5a is connected securely but detachably to the base plate 3.

A swivel plate 5h is arranged on the base part 5a so that it can swivel about the swivel axis 5i in the direction 5k, the swivel plate 5h having two bores with internal threads for receiving a hexagon socket screw 5l in each case. These screws 5l are turned into the internal threads to such a depth that they bear on the base part 5a. The relative inclination between the base part 5a and the swivel plate 5h can be set by the respective screw-in depth of the two opposite hexagon socket screws 5l, as can best be seen from FIG. 2c.

A reference body 5o having longitudinal bores 5q can be connected securely to the swivel plate 5h by means of screws 5r. The longitudinal bore 5q, also referred to as oblong hole, is designed wider than the shank of the screw 5r. With the screws 5r loose, the reference body 5o, on account of the lengthwise extent of the longitudinal bores 5q, can either be displaced in parallel in the direction of movement 5s or can additionally be displaced about the pivot axis 5t in the direction of movement 5u. Thus, the reference body 5o can be arranged displaceably relative to the swivel plate 5h, and in particularly easily offset, and can be securely connected with the aid of the screws 5r. The reference body 5o defines, via the reference surfaces 5p and the forks 5m connected securely to the reference body 5o, the alignment of the system of coordinates X, Y, Z which constitutes the reference coordinate system. As can be seen from FIG. 2c, a guide opening 5z is arranged in the reference body 5o, which guide opening 5z constitutes a longitudinal guide extending in the X direction for a toothed rod 10a. The reference body 5o has a worm gear 5w which is arranged in its interior and which comprises two perpendicular pivot axes 5y, with a knurled screw 5v being arranged on one pivot axis 5y and a worm being arranged inside the reference body 5o, and with a gear 5w being arranged on the other pivot axis 5y and a toothed wheel 5x projecting into the longitudinal guide 5z, which toothed wheel 5x is intended to engage in the toothed rod 10a. The toothed wheel 5x could also be arranged directly on an axis 5y of the knurled screw 5v, so that a worm gear 5w could be dispensed with.

FIG. 3 shows a femur 1 onto which the base plate 3 is screwed. The reference device 5 is connected to the base plate 3 and can be released and removed at any time or put back in place by actuation of the actuating lever 5d. The longitudinal guide 5z extending in the X direction can also be seen in FIG. 3. In a further alternative embodiment, the reference device 5 could also be designed in such a way that, in addition to the swivel axis 5i, it can be swiveled relative to the base part 5a in a direction of movement 5f on a second swivel axis 5j extending perpendicular to the swivel axis 5i, in which case the swivel angle can again be set and fixed by means of screws. Dispensing with the swivel axis 5i, the reference device 5 could also have just the one swivel axis 5j.

Figure 4:
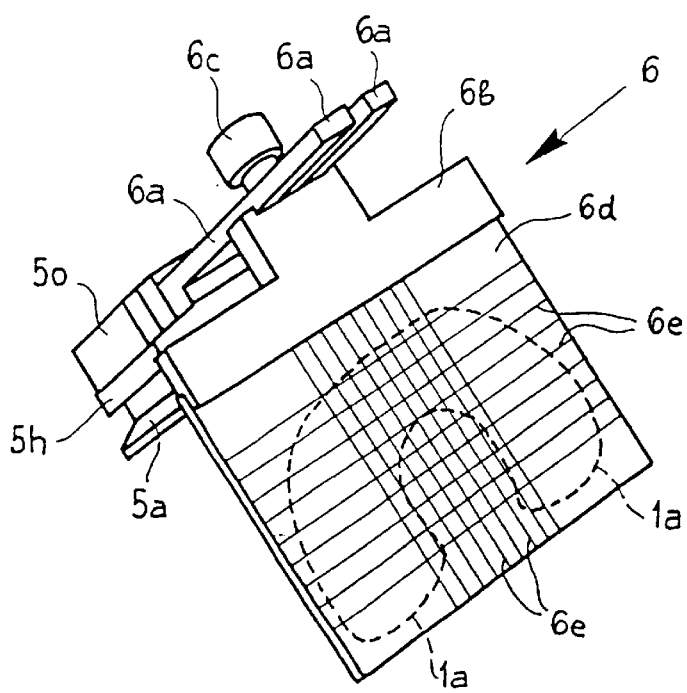
FIG. 4 shows a perspective view of a control jig secured on the reference device.

FIG. 4 is a symbolic representation of the reference body 5o into whose longitudinal guide 5z an insertion and holding part 6a of a control jig 6 is admitted. The control jig 6 comprises a holder 6b with a transparent body 6d arranged thereon, with grid lines 6e. The control jig 6 serves to align the swivel plate 5h in the direction of swiveling 5k. For this purpose, in the arrangement according to FIG. 3, the insert part 6a is introduced into the longitudinal guide 5z and, thereafter, the transparent body 6d with holder 6b, mounted displaceably in the direction of extent of the holding part 6a or in the X direction, is displaced in such a way that the transparent body 6d, as indicated in FIG. 4, comes to lie directly before the femoral condyles 1a. The holder 6b is then fixed on the holding part 6a with the knurled screw 6c. The grid lines 6e in this case extend in the Y and Z directions of the system of coordinates defined by the reference body 5o. By appropriate turning of the screws 5l, the transparent body 6d can be turned about the swivel axis 5i. The position of the transparent body 6d can also be adjusted by displacing the reference body 5o in the direction 5s or in the direction 5u. Thus, the position of the reference body 5o or the system of coordinates can be adjusted in the Y and Z directions with very great precision relative to the position of the condyles 1a.

Figure 15:
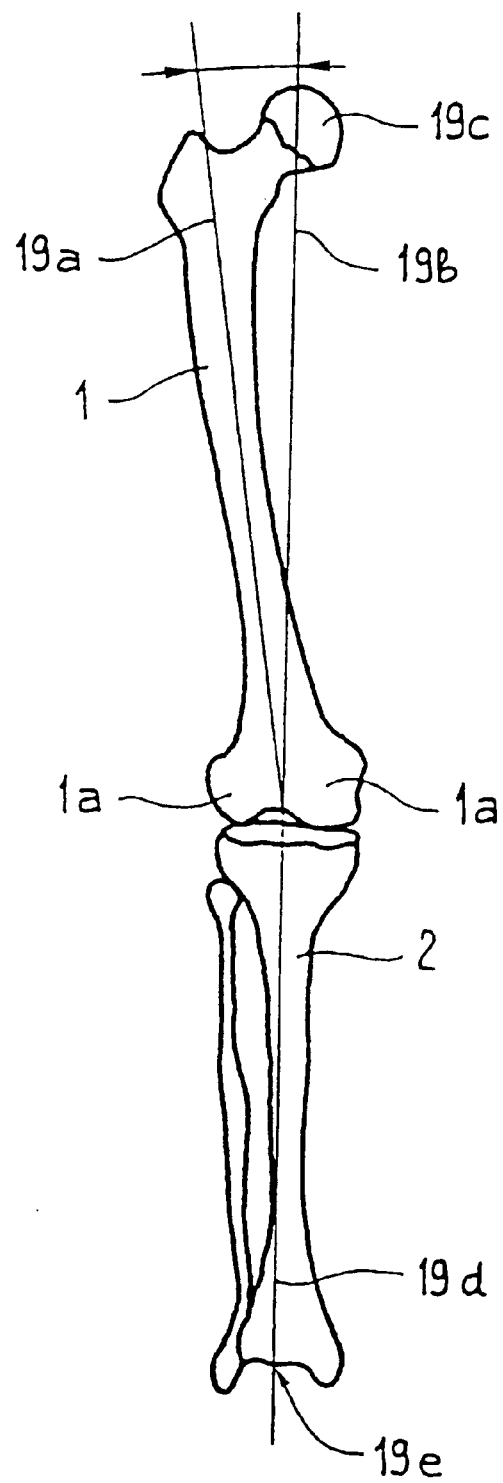
FIG. 15 shows a sagittal view of femur and tibia and their axes.

The weight-bearing axis (WBA) 19b of the femur 1 extends in a known manner, as is shown in FIG. 15, through the center of the head of the hip 19c and through the center of the ankle joint 19e. The anatomical axis 19a of the femur 1 is inclined relative to this weight-bearing axis 19b. The line of the tibia 2 defines a mechanical axis 19d. In the position shown, the femur 1 and the tibia 2 show a flexion of 0°, and the weight-bearing axis 19b and the mechanical axis 19d are congruent.

Figure 5:
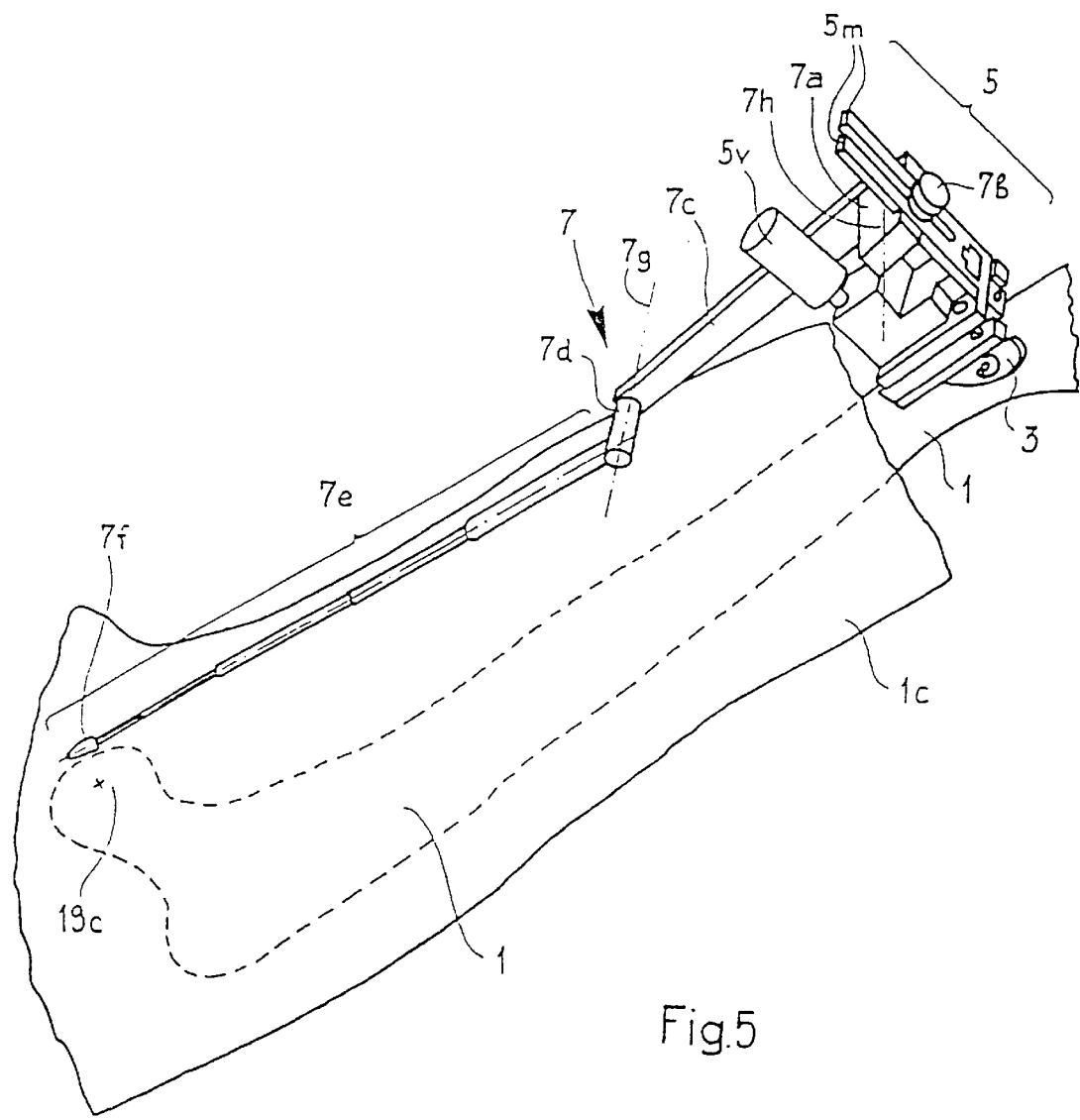
FIG. 5 shows a perspective view of an alignment rod connected to the reference device.

FIG. 5 shows an alignment rod 7 with which it is possible to align the reference body 5o relative to the position of the head of the hip 19c. The alignment rod 7 shall comprise an attachment block 7a which can be secured by means of a knurled screw 7b to the fork 5m. A telescopic rod 7e with end indicator 7f is mounted on the attachment block 7a via the hinge 7d with pivot axis 7g and via the bracket 7c with pivot axis 7h. The alignment rod 7 is designed and is arranged on the reference device 5 in such a way that the telescopic rod 7e extends substantially or as far as possible in the X direction and can be swiveled in the XY plane. The position of the reference body 5o is adjusted, with the screws 5r loose, by means of palpating, for example with the so-called two-finger method, the center of the head of the hip 19c, and the end indicator 7f of the telescopic rod 7e is then placed on the thigh 1c at this position, as a result of which the reference body 5o is aligned such that the projection of the X axis (in the sagittal direction) passes through the center of the head of the hip 19c. In addition, with the aid of the grid lines 6e, it is also possible to adjust the line of the X axis in such a way that the X axis passes through the center of the condyle 1a. Thus, in a sagittal view as shown in FIG. 15, the X axis is congruent to the weight-bearing axis 19b. The screws 5r are tightened and the position of the reference body 5o relative to the swivel plate 5h is thereby fixed. Thus, by aligning the position of the reference body 5o, the reference system or the orthogonal axes in the X, Y and Z directions are defined.

The reference device 5 according to the invention has the advantage that all adjustments effected have been made to the reference device 5 and have as it were been stored in it. It is therefore possible to detach and remove the thereby adjusted reference device 5 from the base plate 3 via the bayonet catch 5b, in order to carry out further maneuvers on femur 1 or tibia 2. At a later stage the reference device 5 can again be secured on the base plate 3, in which case the axes extend in the X, Y and Z directions as previously defined and therefore do not have to be re-set.

An advantage of the reference device 5 is that the course of the axes X, Y and Z can be adjusted very accurately relative to the position of the femur 1 and of the condyles 1a. The reference device 5 could also be made simpler, with adjustment of the reference body 5o relative to the base plate 3 being possible only in one dimension or in two dimensions.

If separability between base plate 3 and reference device 5 is not necessary, then, in a further and simpler embodiment, it is possible for the base plate 3 to be omitted, in which embodiment the base part 5a of the reference device 5 is screwed directly onto the femur 1.

Figure 6:
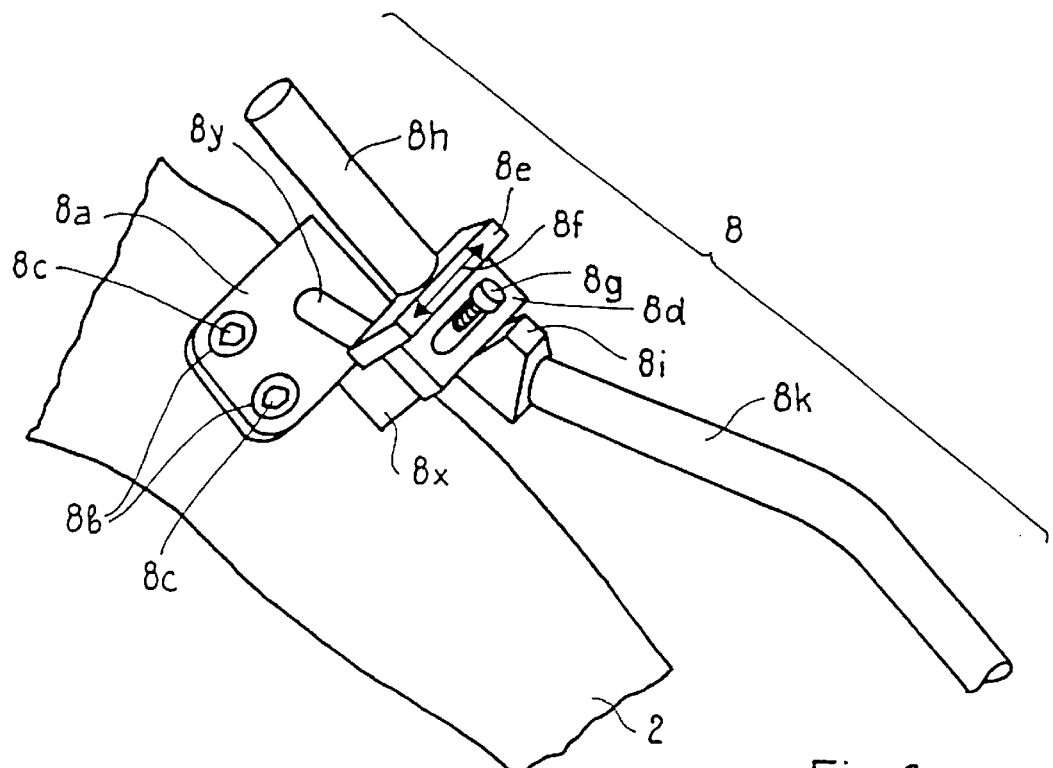
FIG. 6 and FIG. 7 show perspective views of a tibial splint.
Figure 7:
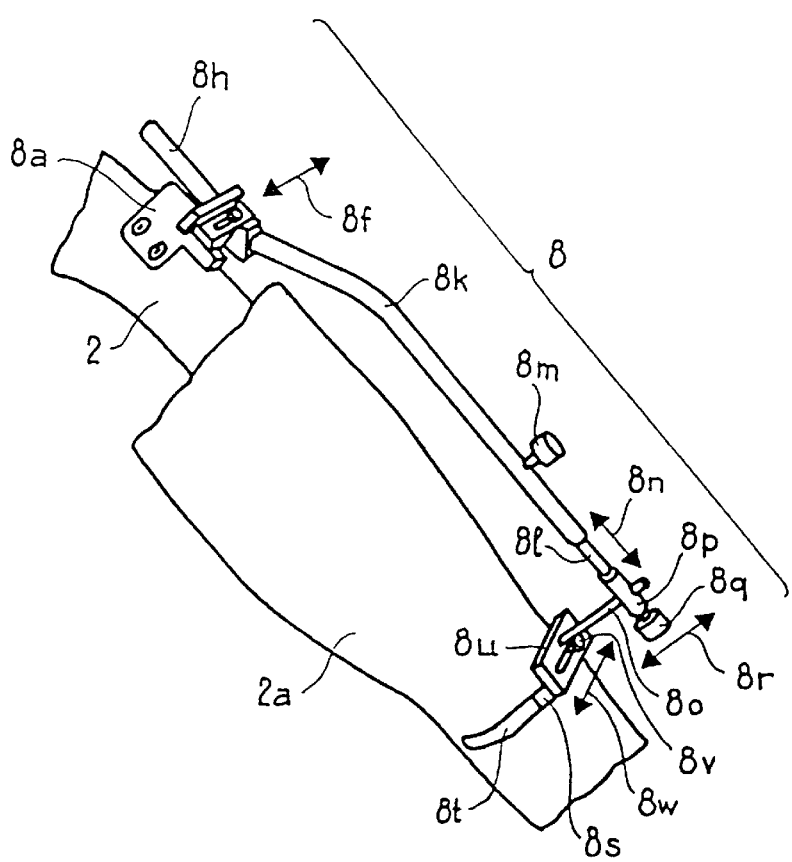
Figure 8:
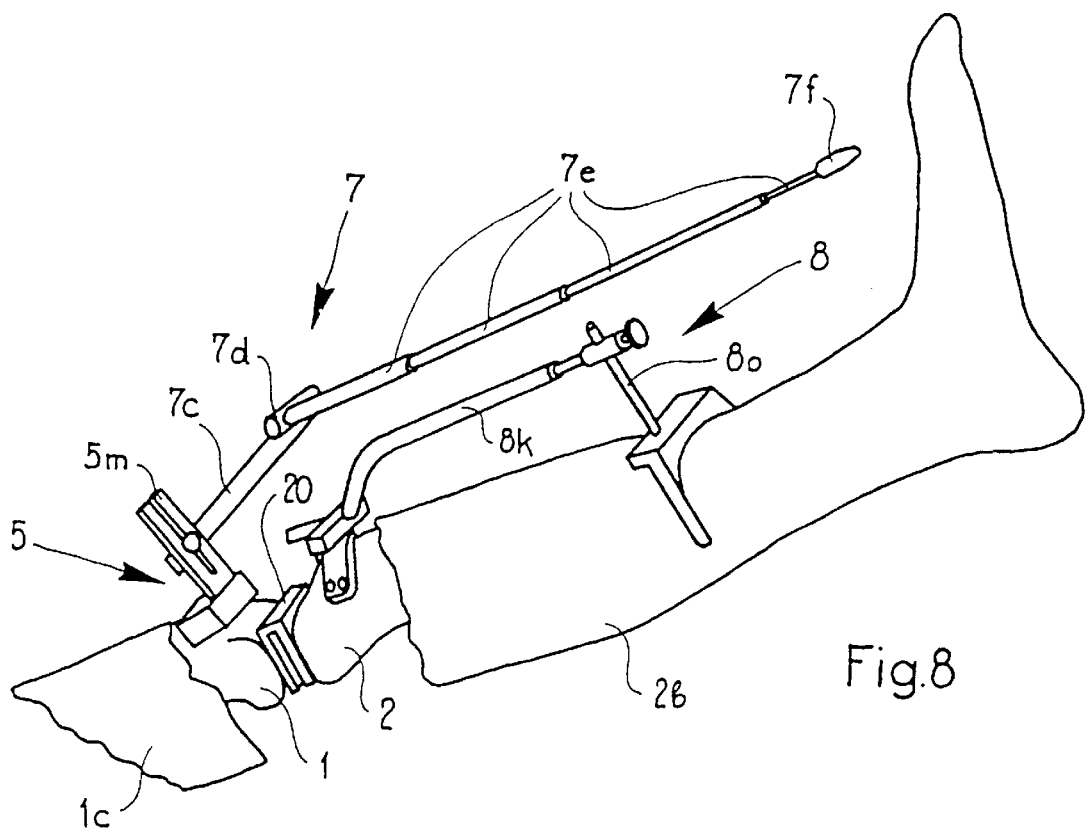
FIG. 8 shows a perspective view of a tibial splint to be checked using the alignment rod.

For aligning the tibia 2, a tibial splint 8 is provided, as illustrated in FIGS. 6 and 7. The tibial splint 8 is preferably secured on the tibia 2 in such a way that the tibial splint 8, in a sagittal view according to FIG. 15, is congruent with the mechanical axis 19d of the tibia 2. A tibial plate 8a having two bores 8b is anchored on the tibia 2 with two bone screws 8c. A bearing part 8d is connected to the tibial plate 8a via a lockable ball joint 8x and the connection part 8y. The ball joint 8x is arranged inside the body designated 8x. A tibial rod 8k opens into an end section 8h via a stop part 8i and a limit stop 8e. In the loosened state, the tibial rod 8k can be displaced in the direction of displacement 8f, and a screw 8g is connected to the bearing web 8d and, when tightened, fixes the tibial rod 8k to the body 8x, as a result of which the position of the tibial rod 8k is fixed in the direction of displacement 8f. At the end remote from the knee joint, a bearing part 8s with bearing 8t is placed on the lower leg 2a and fixed to the latter, for example with the aid of bandages. A displacement part 8u can be displaced relative to the bearing part 8s in the direction of displacement 8w and can be fixed by a screw 8v. The tibial rod 8k opens into a displacement rod 8l which is mounted so that it can be displaced relative to the lengthwise direction 8n of the tibial rod 8k and can be fixed to the tibial rod 8k with the aid of a knurled screw 8m. A pin-shaped holder 8o, which is arranged projecting from the displacement part 8u, can be introduced into a guide part 8p of the displacement rod 8l, can be adjusted in the direction of displacement 8r, and can be fixed with a knurled screw 8g. The described displacement possibilities of the tibial rod 8k relative to the tibial plate 8a and the bearing part 8s allow its course to be adjusted in such a way that the tibial rod 8k, in the sagittal direction, is congruent with the anatomical axis 19d of the tibia 2.

Not later than after the tibial splint 8 has been applied, a tensioning instrument 20, of which an illustrative embodiment is disclosed in the printed specification FR 2 648 699, is inserted between the femur 1 and the tibia 2.

The tensioning instrument 20 is based on the principle of spreader forceps and serves to press the articular surfaces of the tibia 2 and of the femur 1 individually apart at the lateral and medial condyles in such a way that the desired alignment between femur 1 and tibia 2 is obtained. With the device according to the invention, the requirement that the weight-bearing axis 19b of the femur 1 should extend in the direction of the mechanical axis 19d of the tibia 2 can be easily satisfied by the alignment rod 7 indicating the line of the weight-bearing axis 19b being swiveled about the pivot axis 7h to the tibia 2. As the tibial rod 8k indicates the line of the mechanical axis 19d of the tibia 2, the tibia 2 can now be aligned by means of a corresponding adjustment of the tensioning device 20 in such a way that the tibial rod 8k in a sagittal view is congruent with the alignment rod 7. By adjustment to the tensioning device 20, the leg axis can also be set at a slight angle in the varus-valgus direction. It is thus possible intentionally to introduce an angle between the weight-bearing axis 19b and the tibial axis 19d.

If the medial and lateral ligaments do not permit the spreading which is necessary for the desired leg axis position, known surgical interventions must be performed to release the tensioning of the ligaments by means of partial detachment at the points of adhesion to the bone. This must be done until there is suitable ligament tensioning in all flexion positions.

Figure 9:
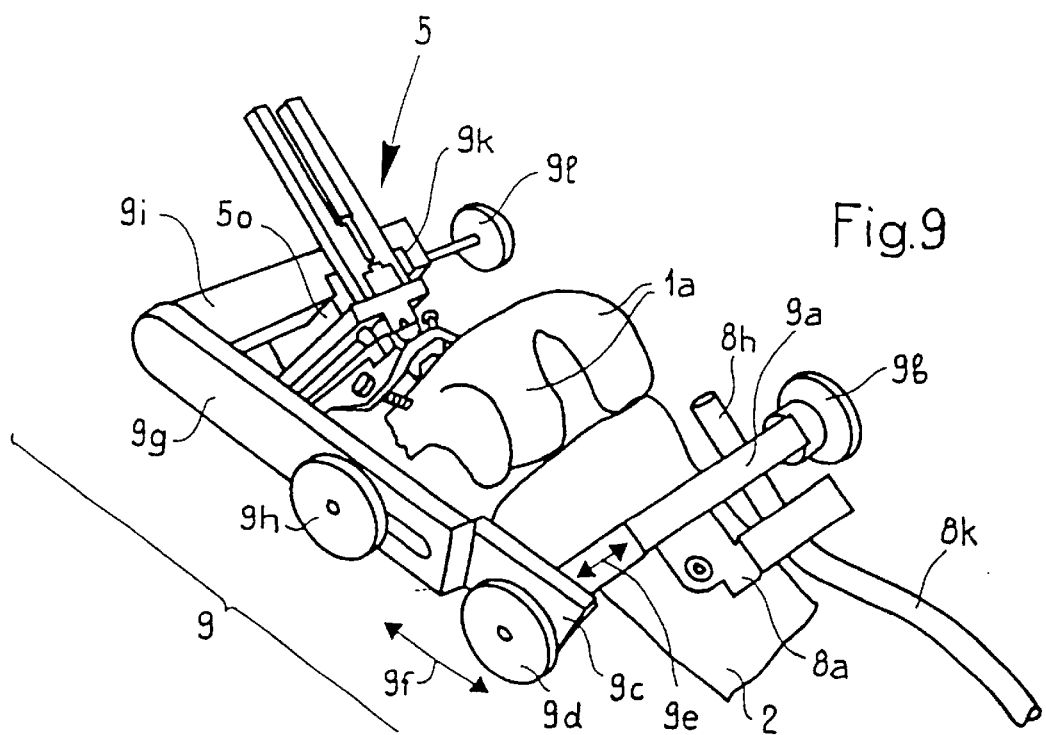
FIG. 9 shows a perspective view of a joint held at 90° flexion with a securing frame.

With the tensioning device 20 in place, the joint is then brought to a position of 90° flexion, as is shown in FIG. 9. In this position, the thigh and the lower leg rest on a suitable support. The femur 1 and the tibia 2 are then fixed relative to each other in this position of 90° flexion with the aid of a U-shaped securing bracket 9. The securing bracket 9 comprises a tibial splint holder 9a via whose knurled screw 9b the end section 8h of the tibial rod 8k can be securely clamped. The securing bracket 9 moreover comprises a bracket base part 9g and a bracket adjustment part 9c which can be adjusted in the longitudinal direction 9f relative to the bracket base part 9g and can be fixed by a knurled screw 9h. The tibial splint holder 9a is connected to the bracket adjustment part 9c in such a way that it can be slid in sliding direction 9e and it can be fixed by the knurled screw 9d. The bracket base part 9g is connected securely to a bracket transverse part 9i which has a recess 9k for bearing on the reference body 5o. The bracket transverse part 9i can be connected securely to the reference body 5o via a knurled screw 9l. The multiple adjustment possibilities of the securing bracket 9 allow the end section 8h of the tibial rod 8k to be connected securely to the reference body 5o in the predetermined position. After this step, the femur 1 and the tibia 2 are held securely in an exactly defined position relative to each other. In this position, the weight-bearing axis 19b and the tibial axis 19d are preferably flush with each other, and the angle enclosed between them is 90 degrees. In a further advantageous embodiment, the securing bracket 9 could also be of rectangular design, with the tibial splint holder 9a and the bracket transverse part 9i each being connected at both ends to a bracket base part 9g and to a bracket adjustment part 9c. Such a rectangular securing bracket 9 has increased stability compared with an embodiment according to FIG. 9.

The tensioning device 20 is then removed and the femur 1 and the tibia 2 are held as shown in FIG. 9. The securing bracket 9 according to the invention has the advantage that the femur 1 and the tibia 2 are held securely in a defined aligned position and that access to the operating field is not obstructed by the U-shaped design of the securing bracket 9.

Figure 10:
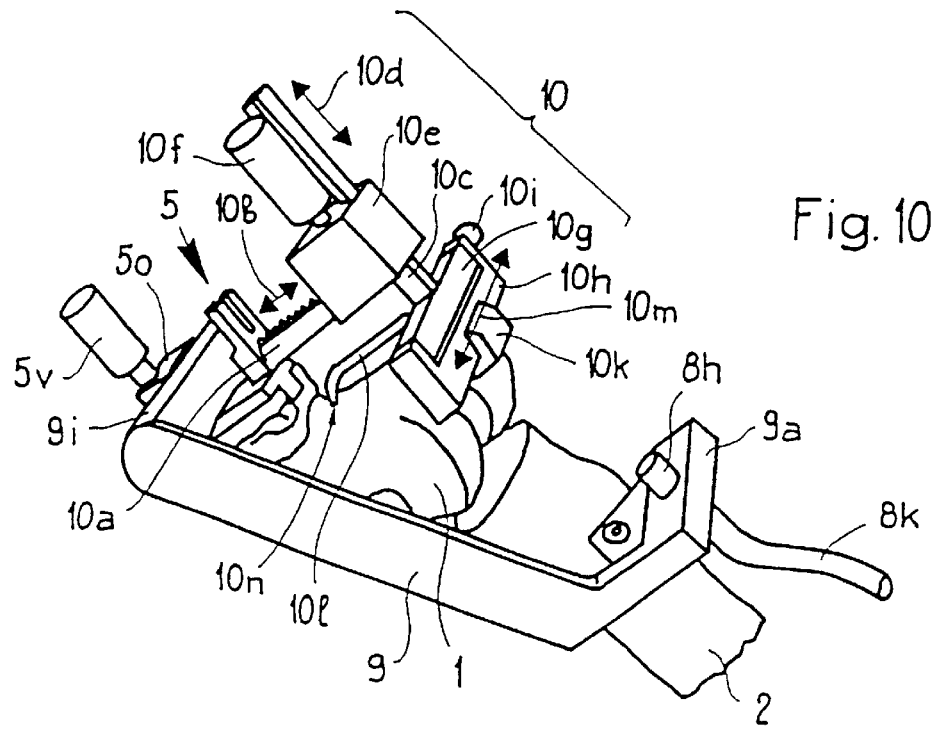
FIG. 10 shows a movement device secured on the reference device.

FIG. 10 shows the arrangement according to FIG. 9, in this case additionally with a movement device 10 arranged on the reference device 5 and allowing a base bar 10g, and adapter parts 10h secured thereon, to be moved in the X and Y directions. The movement device 10, also referred to as an adjustment device or an advance device, comprises an advance device 10e which is connected securely to a toothed rod 10a. This toothed rod 10a is arranged partially extending in the longitudinal guide 5z, the toothed wheel 5x of the knurled screw 5v engaging in the toothed rod 10a in order to move the toothed rod 10a in the direction of displacement 10b which corresponds to the X direction. Like the reference device 5 shown in FIGS. 2a to 2c, the advance device 10e has a knurled screw 10f which drives a worm gear (not shown) which, via a toothed wheel arranged in a longitudinal guide, engages in a toothed rod 10c guided through the longitudinal guide, in order to move this toothed rod in the direction of displacement 10d. In the illustrative embodiment according to FIG. 10, the direction of displacement 10d is identical to the Y direction. The two movement axes or displacement directions 10b, 10d preferably run at right angles to each other, although they can also be at another angle to each other. Advantageously, one direction of displacement 10b runs parallel to the weight-bearing axis 19b, whereas the second direction of displacement lad runs perpendicular to the weight-bearing axis 19b. Instead of being arranged on the reference device 5, the adjustment device 10 could also be arranged on the securing bracket 9, in which case the securing bracket 9 has a longitudinal guide 5z and a knurled screw 5v for receiving and moving the toothed rod 10a.

Figure 12:
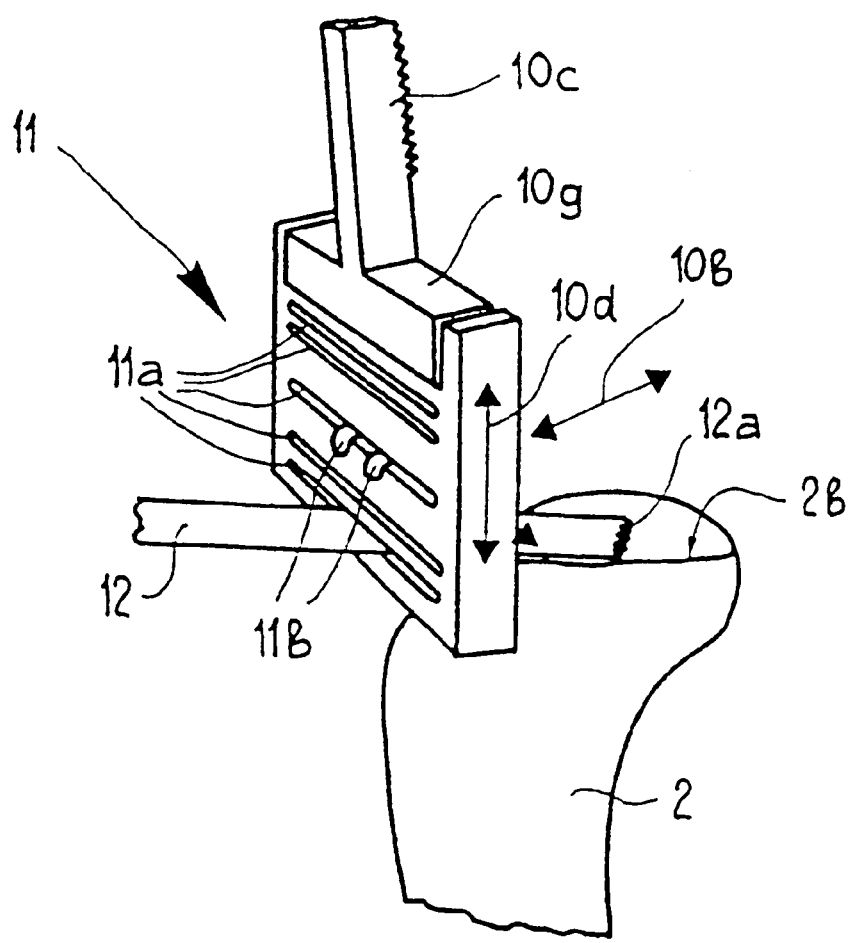
FIG. 12 shows a view of a sawing jig secured on the base bar.

In order to perform the resection of the femur and of the tibia, a sawing jig 11, as is illustrated in FIG. 12, is secured on the base bar 10g of the adjustment device 10, which sawing jig 11 has slots 11a extending at different angles in order to guide the saw blade 12 with saw teeth 12a exactly at the angles predetermined by the implant. FIG. 12 shows a resection cut made with the saw blade 12 on the tibia front 2b. Depending on the design of an endoprosthetic knee-joint, the resection cuts can be made at different angles. For this reason, different sawing jigs 11 are available, with the sawing jig 11 suitable for each particular case being secured on the base bar 10g. The sawing jig 11 additionally has bores 11b for guiding a drill for the patellar channel. The sawing jig 11 can be brought into the required position by manually turning the knurled screws 5v, 10f. The sawing jig 11 is moved exactly parallel, so that exactly parallel resection surfaces can be produced on femur 1 and tibia 2. The toothed rods 10a, 10c could have a scale, for example a scale engraved on the surface, from which scale the distance traveled can be read off. This is advantageous particularly in the case of manual movement or manual actuation of the knurled screws 5v, 10f. The possibility of a manual movement has the advantage that the device can still be used even if a computer or a motor fails, so that the operation can be continued even in such an emergency situation.

Figure 14:
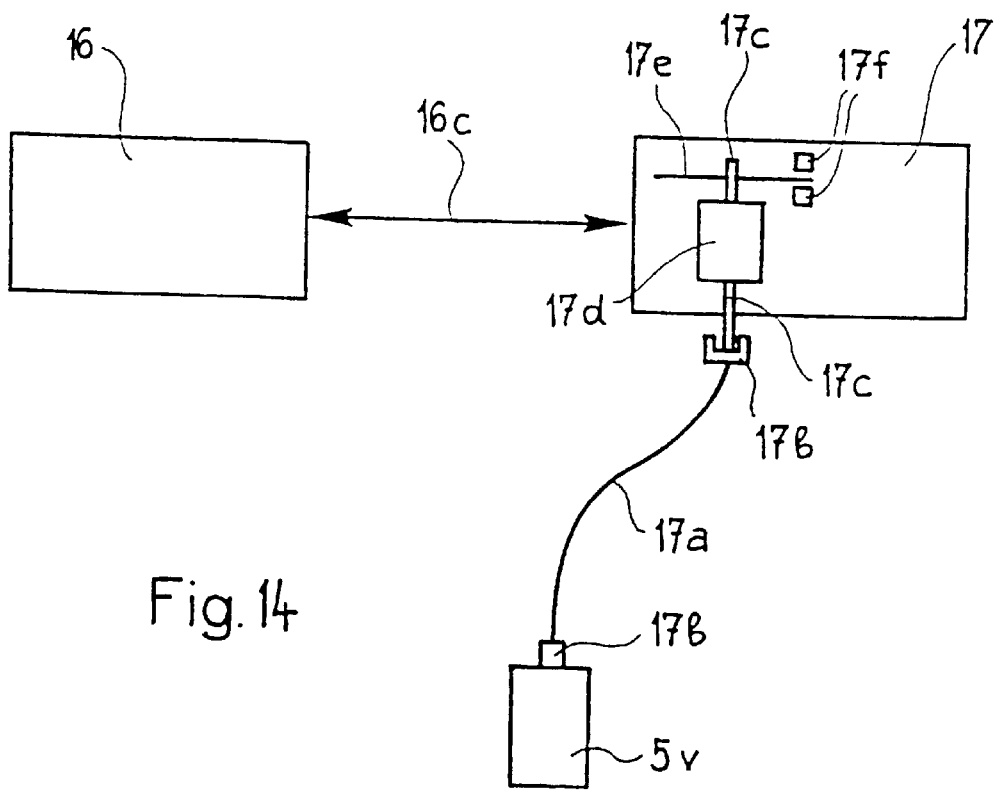
FIG. 14 shows a diagrammatic view of a drive device controlled by a computer.

In a preferred embodiment, the knurled screws 5v, 10f are driven by a motor. FIG. 14 shows a diagrammatic representation of a drive device 17 according to the invention which is connected to and is controlled by a computer 16 via a two-direction data line 16c. The drive device 17 comprises an electric motor 17d with a shaft 17c. Arranged on this shaft 17c there is an angle disk 17e and a sensor 17f for detecting the angle of rotation. The electric motor 17d is controlled by the computer 16 and the angle of rotation of the electric motor 17d is monitored by the computer 16 via the sensor signal 17f. The knurled screw 5v, 10f and the shaft 17c are connected to each other via a flexible shaft 17a which has an adapter part 17b at both ends. The flexible shaft 17a is preferably a metal wire. The arrangement according to FIG. 14 has the following advantages:

Operations on bone entail very strict demands with respect to sterility. For this reason, all objects near the operating field must have sterile properties. It would be considerably complicated to build a sterilizable electric motor which could be arranged directly on the movement device 10. The use of a metal wire, e.g. spring steel wire, has the advantage that the electric motor can be arranged, for example, one to two meters away from the operating field. The use of a spring steel wire string has in particular the advantage of a high modulus of elasticity and a low hysteresis effect. On account of the increased distance from the operating field, there are lesser requirements with respect to the sterility of the drive device 17. The shaft 17a according to the invention additionally has the advantage that it is sterilizable and, since it is easy to produce, can be designed as a disposable product. The drive device 17 also has the advantage that the knurled screw 5v can be driven and its angle of rotation also monitored via the sensor 17f. The drive device 17 can also have a plurality of independent drives for flexible shafts 17a. The shaft 17a can be designed as a solid wire or as a hollow wire. Steel wires are preferably used, but wires of other metals or of plastic or composite material are also suitable. In a further advantageous embodiment, the drive device 17 with electric motor 17d, angle disk 17e and sensor 17f could be arranged in or in place of the knurled screw 5v, in which case the drive device 17 is connected to a computer 16 via an electric control and data line 16c.

In a preferred embodiment, the movement device 10 according to FIG. 10 is driven by a drive device 17 according to FIG. 14, in which the knurled screws 15v, 10f each are connected to a shaft 17a. Thus, it is not only possible to move the base bar 10g, with adapter part 10h secured thereon, in the X and Y directions, but also to measure the geometry of the condyles 1a at selected points as well as the tibial plateau. In the illustrative embodiment according to FIG. 10, a guide 10k for a measurement probe 10l with measurement tip 10n is arranged on the adapter part 10h. The guide 10k is mounted on the adapter part 10h so as to be displaceable in the direction 10m.

Figure 11:
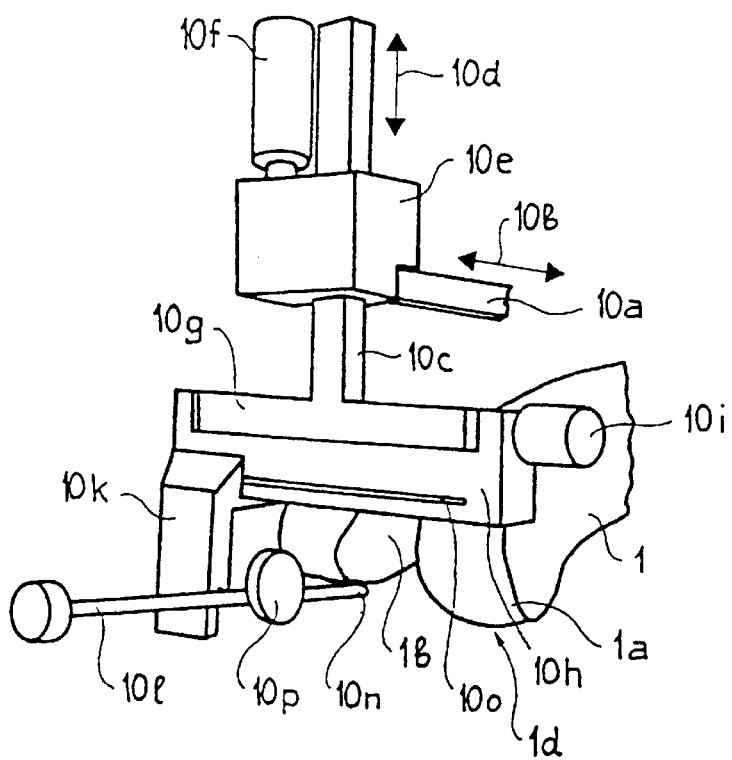
FIG. 11 shows a view of a movement device with a base bar and a measurement bar secured thereon.

The geometry of a femoral condyle 1a can be measured for example in the following manner:

The base bar 10g, initially without an adapter part 10h secured thereon, is moved so that the base bar 10g comes into contact with the femoral condyle 1a on the front of the femur 1. This blocks the rotation of the shaft 17b, which can be detected by the sensor 17f. Thus, the position of the front of the femur 1 can be determined and stored by the computer 16. The base bar 10g is then moved away again and the adapter part 10h with measurement probe 10l is arranged on the base bar 10g, as is shown in FIG. 10. The base bar 10g is then moved until the probe tip 10n of the measurement probe 10l comes to bear on the femur 1 as illustrated. This position is stored by the computer 16. Then, as is shown in FIG. 11, the base bar 10g is moved away again and a further measurement probe 10l is assigned to the guide 10k for the measurement probe and can be secured with a knurled screw 10p. If the measurement probe 10l is arranged in an eccentric position, the dorsal extent 1d of the condyles 1a can be measured by moving the base bar 10g. If the measurement probe 10l is arranged in a central position, the depth of the groove 10b can be measured by moving the base bar 10g. The condyles can also be measured at several points by means of suitable configuration of the measurement probe. The measurement probe 10l according to FIG. 11 could also be used to measure the entire width of the condyles 1a, with the probe tip 10n being brought into medial and lateral contact with the condyles 1a, in which case a scale is advantageously arranged extending on the adapter part 10h in its longitudinal direction and makes it possible to read off the lateral position of the probe tip, so that the total width of the femoral joint head can be determined on the basis of the measured medial and lateral extents of the condyles 1a. This width can be entered in the computer, for example manually, so that the geometric data of the femoral joint head are available to the computer for further calculations.

The measurement probes 10l can be configured in very different ways in order take account of the anatomical shape of the femur and to scan its surface. Thus, a measurement probe 10l could also be designed in such a way that, arranged on the guide 10k similarly to FIG. 11, it allows the dorsal area of the femur 1 to be scanned.

In a preferred embodiment, the overall system for implanting a total endoprosthetic knee joint comprises a computer with a screen. The coordinates of the position of the measurement points of the femoral condyles determined using the measurement probes 10*l* are transmitted to the computer via the drive device 17, in which case the division of the angular wheel 17*e* and also the transmission ratio of the gear of the advance unit 10*e* are preset in the computer, so that the computer can calculate the distances of the individual measurement points in absolute coordinates and preferably in millimeters. A database with the geometric data of available knee-joint implants is also stored in the computer, and the computer compares these data with the measured data and proposes an optimally fitting knee-joint implant and represents this on the screen. In a preferred embodiment, as shown in FIG. 13*a*, the measured femur, the resection lines and the knee-joint implant to be fitted on the femur are illustrated on the screen. The surgeon checks the illustrated proposal and either confirms this proposal, moves the resection lines in their entirety, or chooses another knee-joint implant which appears to him to be more suitable. After the appropriate knee-joint implant has been chosen, the computer accesses a database in which all the geometric data of the implant are stored, in particular including the arrangement and course of the normal bearing surfaces of the implant and the corresponding resection lines. Based on these data, the computer determines which of a plurality of available sawing jigs 11 is to be secured on the base bar 11*g* in order to effect the previously determined cuts. It would be possible to provide just a single sawing jig 11 defining the angles of the respective resection lines. By providing different sawing jigs 11 whose cutting lines are adapted to corresponding implants, the resection lines on the femur can be cut according to the design and size of a particular implant. After the sawing jig 11 has been secured in place, the movement device 10 is driven by the computer in such a way that the sawing jig 11 is moved into the first cutting position. Then, as is shown in FIG. 12, the surgeon can insert the saw blade 12 into the respective slot 11*a* of the jig 11 and effect the cut. After the cut has been made, this can be communicated to the computer 16, for example by actuation of the foot switch 18, whereupon the computer 16 moves the device 10 and the sawing jig 11 to the next cutting position, so that the surgeon can effect the next cut. Since the computer 16 or sawing jig 11 defines precisely both the position of the cut and also its alignment, the resection cuts can be made very precisely according to the geometry of the implant which is to be fitted. This procedure greatly facilitates the work of the surgeon since he no longer has to worry about the position of the cut when cutting and can therefore devote all his concentration on the cut itself, in particular ensuring that no ligaments or other soft tissue parts are damaged during cutting. The device according to the invention also allows a less experienced surgeon to accurately cut the femur 1 and the tibia 2 without any problems and to fit the implant.

Figure 13C:
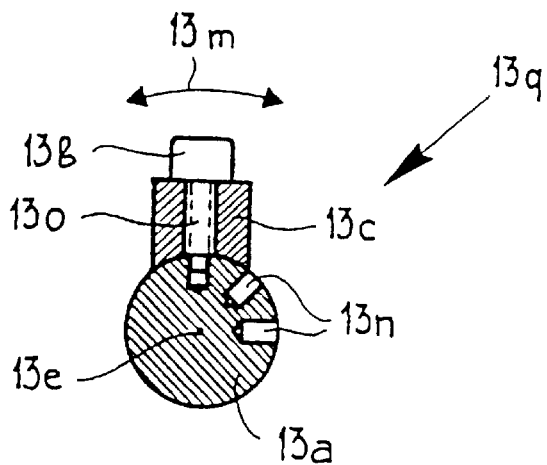
FIG. 13c shows a detail view of a locking device.

FIGS. 13*a*, 13*b*, 13*c* disclose a complete system for implanting a knee prosthesis, which system no longer requires a sawing jig 11 since the position of the sawing device 14 and thus the position of the saw blade 12 are controlled and determined directly by the movement device 10.

As is shown in a side view in FIG. 13*c*, a pivot adjustment device 13*q* designed as a locking device 13*a* is arranged on the base bar 10*g* of the movement device 10. This locking device 13*a* has locking positions 13*n* distributed about its circumference, each locking position 13*n* defining a preset swivel angle of the arm 13*c* in the direction of swiveling 13*m*. A knurled screw 13*b* allows the screw shank 13*o* to be raised and lowered. The pivot adjustment device 13*q* could also have, instead of the locking device 13*a*, a drive motor making it possible to set a predeterminable pivot angle. Such a motor-driven pivot adjustment device 13*q* preferably also comprises a pivot angle sensor which detects the pivot angle so that the angle, to be assumed, of the pivot adjustment device 13*q* can be preset, for example, with the aid of a control device or a computer. As is shown in FIG. 13*b*, the arm 13*c* is connected to a second arm 13*f* via a hinge moving in the direction of movement 13*d*, which second arm 13*f* is in turn connected to the third arm 13*h* via a hinge moving in the direction of movement 13*g*. The third arm 13*h* forms on the one hand an axial attachment 13*i* for the sawing device 14 and on the other hand a guide 13*k* with slot 13*l* for the saw blade 12. The holding arm 13 thereby formed allows the saw blade 12 to be guided or swiveled in one plane, preferably in the saw blade plane. The saw blade 12 forms a saw blade plane and is mounted so as to be displaceable in this plane. The arm 13 can be designed such that it has a spring force, so that when the saw blade 12 is brought toward the condyle 1*a*, an increasing restoring force acts on the sawing device 14. In order to generate such a spring force, torsion springs for example could be arranged in the hinges of the arm 13. In the illustrative embodiment shown, the guide 13*k* is connected securely to the arm 13*h*. However, the guide 13*k* could also be articulated on the arm 13*h* via a hinge, so that the guide 13*k* could be swiveled toward the attachment 13*i*. By means of this measure, the saw blade 12 can penetrate deeper into the body which is to be cut.

The sawing device 14 has a hand grip 14*a* which, in order to reduce excessive torques caused by the maneuvering, can be swiveled in the direction 14*g* about the axis 14*h* relative to the holding arm 13. The hand grip 14*a* could also be mounted so as to swivel about a pivot axis 13*p*. The hand grip 14*a* thus serves to initiate movement in the direction 14*c* and in the direction of swiveling 14*d* about the axis 13*p*. As a result, the position of the hand grip 14*a* in the vertical direction of swiveling is independent of the position of the saw blade 12. As is shown in FIG. 13*c*, the holding arm 13 can be inclined relative to the base bar 10*g* by turning the arm 13*c* about the pivot axis 13*e* of the locking device. Otherwise the position of the saw blade 12 is determined by the movement device 10 controlled by the computer 16. Since the saw blade 12 is designed relatively long in the direction of extent 14*c*, the guide 13*k* is preferably provided with a slot 13*l* in order to guide the relatively thin saw blade 12 in a defined position and in order to avoid bending of the saw blade 12. Since the holding arm 13 together with the sawing device 14 could exert relatively great forces on the movement device 10 or base plate 3, a frame 15 is provided in the illustrative embodiment shown in FIG. 13*a*, which frame 15 comprises a cable winder device 14*f* and a cable 14*e* which has the task of generating a counterforce F compensating at least for the force of gravity of the sawing device 14. The frame 15 comprises a boom 15*a*, a vertical bar 15*b*, an underframe 15*c* and wheels 15*d*. The device 14*b* for controlling the sawing device 14 is also arranged on the frame 15. The computer 16 with screen 16*a* and keyboard 16*b* is also secured on the frame 15. The drive device 17 is additionally secured on the frame 15, the two knurled screws 5*v*, 10*f* being driven via the flexible shaft 17*a* from the drive device 17.

The holding arm 13 shown could also be designed with sensors making it possible to detect the angles in the movement directions 13*d*, 13*g* and 13*m* in order to determine the exact position of the saw blade 12 or in order to measure the position and geometry of the condyle 1*a* with a probe head arranged in place of the saw blade 12.

FIGS. 16*a* to 16*d* disclose a further illustrative embodiment of a base plate 3 or base device 3 which can be anchored on the femur 1. This base device 3 comprises a base platform 3*h*, with longitudinal axis 3*s*, on which four legs 3*i*, 3*k* are arranged so as to be displaceable in direction 3*l*. The legs 3*i*, 3*k* can be displaced on grooves 3*o* extending in direction 3*l*. A shaft 3*n* with external thread engages in an internal thread of the legs 3*i*, 3*k*. The shaft 3*n* has a screw head 3*p* which is accessible from the side. The thread in the leg 3*i* is designed as a lefthand thread, and the thread in the leg 3*k* is designed as a righthand thread, with the thread of the shaft 3*n* being adapted accordingly for engagement. Thus, while the screw head 3*p* is being turned, two legs 3*i*, 3*k* arranged alongside each other in each case move either toward each other or away from each other. The shaft 3*n* has, at the center, a cylindrical part section 3*m* which is greater than the diameter of the shaft 3*n* and which is arranged in an interspace 3*r* of the base platform 3*h*, and which, in displacement direction 3*l*, bears on the base platform 3*h* with slight play on each side and thus fixes the position of the shaft 3*n* relative to the base platform 3*h* in direction 3*l* and therefore serves as centering element 3*m*. FIG. 16*b* is a side view showing two opposite legs 3*i*, 3*k* which, on the opposing inner surfaces, have tips 3*q* which project in displacement direction 3*l* and are intended to penetrate into the femur 1. As is shown in FIG. 16*d*, the base device 3 is secured on the femur 1 by means of this device initially being placed on the femur 1 in the line of extent of the femoral axis 19*a*, and the opposite legs 3*i*, 3*k* then being moved toward each other by turning the shaft 3*n* until the tips 3*q* penetrate into the femur 1 and the base device 3 is firmly connected to the femur 1. In an advantageous embodiment, the shaft 3*n* has a screw head 3*p* at both ends, so that the shaft 3*n* can be optionally actuated from either of the two legs 3*i*, 3*k*. An advantage of the illustrated embodiment of a base device 3 is that after it has been secured on the femur 1 it extends in the direction of the femoral axis 19*a* and in the direction of the intramedullary cavity of the femur 1. Thus, the base device 3 has an intramedullary line of direction, but without using an intramedullary body.

The two recesses 3*b*, 3*f* are designed in the same way as in the base plate 3 according to FIG. 1*a* and serve to secure the reference body 5 by means of a bayonet catch. FIG. 16*c* is a plan view showing the arrangement of the recesses 3*b*, 3*f* on the base platform 3*h*. The two lower recesses 3*b*, 3*f* define a straight line 19*b* which intersects, at an angle α, the straight line 19*a*, 3*s* running through the center of the base platform 3*h*. This angle α is preferably in the range of 6±2 degrees. With the base device 3 secured on the femur 1, the straight line 19*a* corresponds to the line of the anatomical axis 19*a* of the femur 1. Statistical studies have shown that the weight-bearing axis 19*b* deviates by approximately 6 degrees from the line of the anatomical axis 19*a*, so that the axis 19*b* shown in FIG. 16*c* corresponds approximately to the line of the weight-bearing axis 19*b* when the base device 3 is fixed on the femur 1. The base device 3 has two pairs of recesses 3*b*, 3*f*, the pair arranged above the straight line 19*a*, 3*s*, as shown in FIG. 16*d*, being used on the femur 1 of a right leg, and the lower pair being used on the femur 1 of a left leg, in order to approximately define the line of the weight-bearing axis 19*b* when the anatomical axis 19*a* of the femur 1 has been determined.

What is claimed is:

1. A device for localizing and executing resection cuts on a femur (1) for preparing an implantation of a total endoprosthetic knee joint, comprising a reference device (5) releasably attachable to a distal area of the femur (1), alignment of the reference device relative to the femur (1) being accurately positionable, an adjustment device (10) connected to the reference device (5) being movable relative to the reference device and provided with a linearly movable base part (10*g*) for the attachment of an instrument, a first drive device (5*v*, 21) for linearly moving the adjustment device (10) relative to the reference device (5) in a direction (10*b*) of a first axis (X) of a system of coordinates (X, Y, Z), a second drive device (10*f*, 17) for linearly moving the base part (10*g*) in a direction (10*b*) of another axis (y) of the system of coordinates (X, Y, Z), both the first and second drive devices comprising a motor drive.

2. A device according to claim 1, wherein both the first and second drive devices comprise an electromotive drive (17*d*).

3. A device according to claim 2, wherein the electromotive drives (17*d*) are controlled by a computer (16), to which a screen (16*a*) and an input keyboard (16*b*) are assigned.

4. A device according to claim 1, wherein the reference device (5) determines at least the first axis (X) as extending essentially in the direction of a weight-bearing axis (19*b*) of the femur (1) when the reference device (5) is aligned relative to the femur.

5. A device according to claim 4, wherein the adjustment device (10) determines the second axis (Y), the first and second axes (X, Y) extending perpendicular to each other and enclosing a plane in which the weight-bearing axis (19*b*) essentially lies.

6. A device according to claim 1, wherein the reference device (5) has a linear guide (5*z*) extending in the direction (10*b*) of the first axis (X) of the system of coordinates (X, Y, Z), the adjustment device (10) comprises a rod which fits into the linear guide (5*z*) and can be displaced in the direction of the first axis (X), and the first drive device (5*v*, 21) acts on the rod (10*a*) and permits a movement of the rod (10*a*) relative to the reference device (5).

7. A device according to claim 6, wherein the rod is a toothed rod.

8. A device according to claim 1, wherein at least one measurement sensor (10*l*) is arranged detachably on the base part (10*g*) of the adjustment device (10) in order to detect the position of the condyles (1*a*) of the femur (1).

9. A device according to claim 1, wherein an anchoring part (3) is provided which can be attached securely on the femur (1), and in that the anchoring part (3) and the reference device (5) together form a releasable catch.

10. A device according to claim 9, wherein the anchoring part (3) comprises a base platform (3*h*) with a longitudinal axis (3*s*) and at least two legs (3*k*, 3*i*) mounted displaceably relative to the base platform (3*h*) and arranged opposite each other approximately perpendicular to the longitudinal axis (3*s*), the legs (3*k*, 3*i*) having projecting points (3*q*) arranged extending toward the femur (1) and capable of penetrating into a femoral bone.

11. A device according to claim 9, wherein the anchoring part (3) has a three-point support (3*a*) which is intended to bear of the femur (1).

12. A device according to claim 9, wherein the releasable catch is a bayonet catch.

13. A device according to claim 1, wherein the reference device (5) has a base part (5*a*) which can be detachably fixed in the distal area of the femur (1), and a reference body (5*o*) is connected to the base part (5*a*), whose alignment can be accurately positioned relative to the femur (1).

14. A device according to claim 13, wherein an actuating means (5*l*, 5*r*) acting between the reference body (5*o*) and the base part (5a) is provided for fixing a mutual position between the reference body and the base part.

15. A device according to claim 13, wherein the base part (5a) is mounted to pivot relative to the reference body (5o) at least about an axis (5i) which extends essentially in the direction of a weight-bearing axis (19b) of the femur (1) when the base part (5a) is fixed on the femur.

16. A device according to claim 13, wherein the reference body is connected to the base part in one of an articulated and displaceable manner.

17. A device according to claim 1, wherein an alignment rod (7) is mounted extending along the first axis (X) and can pivot about a pivot axis extending in another direction (Z) of another axis of the system of coordinates (X, Y, Z) on the reference body (5o).

18. A device according to claim 1, wherein the first drive device (5v, 21) is arranged directly on the reference device (5).

19. A device according to claim 1, wherein the first drive device (5v, 21) is arranged at a distance from the reference device (5) and is operationally connected to the reference device (5) via a flexible shaft (17a).

20. A device according to claim 1, wherein the second drive device (10f, 17) is arranged directly on the adjustment device (10).

21. A device according to claim 1, wherein the second drive device (10f, 17) is arranged at a distance from the adjustment device (10) and is operationally connected to the adjustment device (10) via a flexible shaft (17a).

22. A device according to claim 1, wherein a sawing jig (11) for guiding a saw blade (12) is secured on the base part (10g) of the adjustment device (10).

23. A device according to claim 1, wherein a cutting device (14) is secured on the base part (10g) of the adjustment device (10).

24. A device according to claim 23, wherein the cutting device is a sawing device (14) having a saw blade (12).

25. A device according to claim 24, wherein the saw blade (12) of the sawing device (14) defines a saw blade plane, the sawing device (14) is secured with a connection means (13) on the base part (10g) of the adjustment device (10), the connection means (13) and the sawing device (14) being designed so that the saw blade (12) is mounted to be displaceable exclusively in the saw blade plane.

26. A device according to claim 25, wherein the connection means (13) is designed as one of a swivel arm (13f, 13h) and a double-axis telescopic guide.

27. A device according to claim 25, wherein a hand grip (14a) is articulated on the sawing device (14) to assume different spatial positions whereby the spatial position of the hand grip (14a) does not influence alignment of the saw blade (12) relative to a cutting plane.

28. A device according to claim 25, wherein the connection means (13) is connected to the base part (10g) of the adjustment device (10) via a pivot adjustment device (13q) having a pivot axis (13e), and in that the pivot adjustment device (13q) permits swiveling of the connection means (13) relative to the adjustment device (10) about a pivot angle (13m).

29. A device according to claim 28, wherein the pivot adjustment device is designed as a mechanical locking device (13q) which has stop elements (13b, 13o) in order to stop the pivot angle of the pivot axis (13e) in predetermined positions.

30. A device according to claim 28, wherein the pivot adjustment device (13q) comprises a drive motor making it possible to set a predetermined pivot angle.

31. A device according to claim 30, wherein the pivot adjustment device includes a pivot angle sensor to detect the pivot angle.

32. A method for performing resection cuts on a femur (1) comprising: fixing a reference device (5) on a distal end of the femur (1), aligning the reference device relative to a direction of extent of the femur (1), displaceably connecting a sawing jig (11), for guiding a saw blade (12), to the aligned reference device (5), guiding the saw blade guided in the sawing jig in an alignment position defining the direction of extent of a resection cut to be made, carrying out the resection cut with the saw blade (12) guided in the alignment position.

* * * * *